United States Patent [19]

Baum

[11] 4,254,052

[45] Mar. 3, 1981

[54] PREPARATION OF ESTERS

[75] Inventor: Jonathan S. Baum, Pennington, N.J.

[73] Assignee: FMC Corporation, Philadelphia, Pa.

[21] Appl. No.: 159,338

[22] Filed: Jun. 13, 1980

Related U.S. Application Data

[63] Continuation-in-part of Ser. No. 079,610, Sep. 27, 1979, abandoned.

[51] Int. Cl.³ .................. C07C 120/00; C07C 121/75
[52] U.S. Cl. ........................................... 260/465 D
[58] Field of Search .................................. 260/465 D

[56] References Cited

U.S. PATENT DOCUMENTS

| 3,835,176 | 9/1974 | Matsuo et al. | 260/465 D |
| 4,024,163 | 5/1977 | Elliott et al. | 260/465 D X |
| 4,072,677 | 2/1978 | Callander | 260/239.1 |
| 4,110,362 | 8/1978 | Sheldon et al. | 260/465 D |

FOREIGN PATENT DOCUMENTS

| 54-142046 | 11/1979 | Japan . |
| 1439615 | 6/1976 | United Kingdom . |
| 2000764 | 1/1979 | United Kingdom . |

*Primary Examiner*—Dolph H. Torrence
*Attorney, Agent, or Firm*—Richard L. Hansen; Henry R. Ertelt

[57] ABSTRACT

Certain alpha-cyano esters are prepared by reacting an acyl halide with an aldehyde in a substantially water-immiscible aprotic solvent and an aqueous solution of water-soluble cyanide salt in the presence of a rate-promoting agent selected from acid salts of tertiary amines.

7 Claims, No Drawings

PREPARATION OF ESTERS

This is a continuation in part of Application Ser. No. 079,610, filed Sept. 27, 1979, abandoned.

This invention relates to a process for preparing esters of carboxylic acids, more specifically, esters which contain a cyano group bonded to the alpha-carbon atom in the alcohol portion of the ester molecule.

Esters with a cyano group so situated are prepared by reacting an acid with the appropriate cyanohydrin. According to U.S. Pat. No. 3,835,176, the reaction can also be effected by treating an acyl halide with a mixture of the appropriate aldehyde and aqueous sodium or potassium cyanide, optionally in an aprotic solvent. It is disclosed, for example, that 3-phenoxy-α-cyanobenzyl chrysanthemate is prepared in 64% yield by reacting chrysanthemoyl chloride, 3-phenoxybenzaldehyde, and an aqueous solution of sodium cyanide at 0° C. for 1 hour.

U.S. Pat. No. 4,110,362 discloses a variation of this process which employs, in addition to the acyl halide, the aldehyde, and the water-soluble cyanide, a mixture of water, a water-immiscible aprotic solvent, and an "onium," e.g., a quaternary ammonium, catalyst. This variation shortens the reaction time and increases the yield sufficiently to make the process a candidate for the commercial production of insecticidal esters. Insecticidal alpha-cyano esters whose preparations could be facilitated include α-cyano-3-phenoxybenzyl 3-(2,2-dichloroethenyl)-2,2-dimethylcyclopropanecarboxylate and α-cyano-3-phenoxybenzyl 3-(2,2-dibromoethenyl)-2,2-dimethylcyclopropanecarboxylate, whose insecticidal activity is disclosed in U.S. Pat. No. 4,024,163, incorporated by reference herein. Other insecticidal alpha-cyano esters of particular interest are α-cyano-3-phenoxybenzyl 3-(2-chloro-3,3,3-trifluoropropenyl)-2,2-dimethylcyclopropanecarboxylate, α-cyano-3-phenoxybenzyl 2,2,3,3-tetramethylcyclopropanecarboxylate, and α-cyano-3-phenoxybenzyl 2-(4-chlorophenyl)-3-methylbutanoate, whose activity is disclosed in Great Britain Pat. No. 2,000,764, U.S. Pat. No. 3,835,176, and Great Britain Pat. No. 1,439,615, respectively, all of which are incorporated herein by reference. However, the onium catalysts are relatively expensive.

One advantage of the instant invention is that it provides a process for making alpha-cyano esters in very high yield in a short time and employs inexpensive catalysts. Another advantage of this invention is that it provides an esterification process whose product does not require lengthy and expensive purification.

Accordingly, this invention provides a method to prepare an insecticidal alpha-cyano ester by reacting an acyl halide with an aldehyde in a mixture of substantially water-immiscible aprotic solvent and an aqueous solution of water-soluble cyanide salt in the presence of a catalytic amount of rate-promoting agent selected from acid salts of tertiary amines. Either the acyl halide or the aldehyde may exhibit optical or geometric isomerism, which is not affected by the reaction.

In a preferred embodiment, there is provided a process for preparing an insecticidal α-cyano-3-phenoxybenzyl ester of the formula

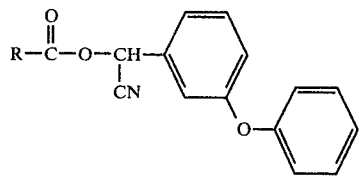

wherein R is selected from 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, 2,2,3,3-tetramethylcyclopropyl, and 1-(4-chlorophenyl)-2-methylpropyl which comprises reacting an acyl halide of the formula

wherein X is chlorine or bromine and R is as defined above with 3-phenoxybenzaldehyde in a mixture of substantially water-immiscible aprotic solvent and an aqueous solution of water-soluble cyanide salt in the presence of a catalytic amount of rate-promoting agent selected from acid salts of tertiary amines.

The process of this invention is especially effective in producing a high yield of insecticidal α-cyano-3-phenoxybenzyl esters in a short time when R is 3-(2,2-dichloroethenyl)-2,2-dimethylcyclopropyl, 3-(2,2-dibromoethenyl)-2,2-dimethylcyclopropyl, or 3-(2-chloro-3,3,3-trifluoropropenyl)-2,2-dimethylcyclopropyl, and outstanding results are obtained when R is 3-(2,2-dichloroethenyl)-2,2-dimethylcyclopropyl.

Although the process of this invention is especially advantageous when R is selected from the groups named above, the process is also effective in producing other alpha-cyano esters wherein R is an aliphatic or aromatic group, which may optionally contain various substituents. Although the process of this invention is preferably employed to produce α-cyano-3-phenoxybenzyl esters by using 3-phenoxybenzaldehyde as a reactant, the process is equally suited to the production of other alpha-cyano esters by varying the type of aldehyde employed in the process.

Various aprotic solvents which are substantially water-immiscible may be used in the process. Any alkyl, haloalkyl, aryl, haloaryl, aralkyl, haloaralkyl, or cyclic hydrocarbon, provided that it is a liquid at temperatures between about 0° C. and 50° C. and forms a discrete second phase when mixed with water, may be used. Such solvents include iso-hexane, 3-methylpentane, 2,3-dimethylbutane, 2,2-dimethylbutane, n-heptane, n-octane, petroleum ether, ligroin, n-propyl bromide, n-propyl iodide, n-butyl chloride, n-butyl bromide, n-pentyl chloride, n-pentyl bromide, diethyl ether, dipropyl ether, dibutyl ether, benzene, toluene, and xylene, for example. Among these solvents, n-heptane is preferred because it is readily available and inexpensive.

A number of water-soluble cyanide salts may be used; for example, the salt may be an alkali metal cyanide such as lithium, sodium, potassium, rubidium, or cesium cyanide, or mixtures thereof. Among these, sodium cyanide generally is preferred.

The cyanide salt is dissolved in water, the amount of water employed being relatively small, but preferably sufficient to keep all of the cyanide salt in solution under the reaction conditions. In the case that the salt is sodium cyanide, the preferred molar ratio of water to sodium cyanide is between about 3.5 and 6, preferably about 4.5.

The process of this invention is conducted in the presence of a catalytic amount of rate-promoting agent selected from acid salts of tertiary amines. For purposes of this invention, a catalytic amount of rate-promoting agent is in the range 1-5 mole percent based on aldehyde, advantageously about 2 mole percent.

The tertiary amines whose acid salts are rate-promoting agents contain one or more, e.g., two, nitrogen atoms. For purposes of this invention and wherever it appears in the specification or claims the term, "acid salts of tertiary amines," means products of the reaction between a strong acid, such as HCl, HBr, $H_2SO_4$, HBF$_4$, HClO$_4$, or HCN and a tertiary amine or polyamine, a tertiary polyamine being a compound containing more than one tertiary amino nitrogen atom.

For purposes of this invention, a tertiary amine has the structural formula

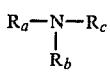

wherein $R_a$, $R_b$, and $R_c$ are hydrocarbon groups.

Particularly desirable tertiary polyamines within the scope of this invention are linear tertiary polyamines of the formula

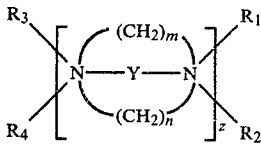

wherein Y is —(CH$_2$)$_k$— with k being 1-6, C$_3$-C$_7$ cycloalkane, C$_2$-C$_6$ alkenyl, or C$_2$-C$_6$ alkynyl; z is 1 or 2, and when z is 1, m and n are 0 or independently 1-6, and when m and n are 0, R$_1$, R$_2$, R$_3$, and R$_4$ are hydrocarbon groups, and R$_1$ may be joined with R$_2$, and R$_3$ may be joined with R$_4$ to form a ring containing the N atom to which both are joined, and when m is 1-6 and n is 0, R$_1$ and R$_3$ are absent, and R$_2$ and R$_4$ are hydrocarbon groups, and when both m and n are at least 1, R$_2$ and R$_4$ are absent; and when z is 2, m and n are 0, R$_1$ and R$_3$ are hydrocarbon groups and R$_2$ and R$^4$ are absent.

Particularly useful linear tertiary polyamines within the aforesaid description are 2,4-dimethyl-2,4-diazapentane, 2,5-dimethyl-2,5-diazahexane, 1,1'-(1,2-ethanediyl)bis[piperidine], N,N,N',N'-tetramethyl-1,2-diaminocyclohexane, 1,4-dimethyl-1,4-diazacyclohexane, diazabicyclo[2.2.2]octane, 2,6-dimethyl-2,6-diazaheptane, 2,7-dimethyl-2,7-diazaoctane, 2,7-dimethyl-2,7-diaza-4-octene, 2,7-dimethyl-2,7-diaza-4-octyne, 2,9-dimethyl-2,9-diazadecane, and 2,5,8,11-tetramethyl-2,5,8,11-tetraazadodecane. Among these compounds, diazabicyclo[2.2.2]octane, 2,6-dimethyl-2,6-diazaheptane, 2,7-dimethyl-2,7-diazaoctane, and 2,5,8,11-tetramethyl-2,5,8,11-tetrazadecane are preferred, and diazabicyclo[2.2.2]octane is especially attractive.

Macrocyclic tertiary polyamines such as 1,4,8,11-tetraazacyclotetradecane, for example, are also useful, as are sparteine and hexamethylenetetraamine.

Although other acid salts are effective, it is preferred that the salt be a hydrohalide, especially a hydrochloride. Acid salts of tertiary amines which may be employed in this invention include, for example, diazabicyclo[2.2.2]octane dihydrochloride, 2,7-dimethyl-2,7-diazaoctane dihydrochloride, 2,3,4,6,7,8,9,10-octahydropyrimido[1,2-a]azepine hydrochloride, and quinuclidine hydrochloride.

The process of this invention is carried out between approximately equimolar amounts of the acyl halide, preferably the acyl chloride, aldehyde and aqueous solution of cyanide salt in the water-immiscible aprotic solvent, but slight excesses of the acyl halide and cyanide salt are typically used. The acyl halide may be added last, preferably dropwise, to the stirred reaction mixture, but it is preferred to add a solution containing aldehyde and acyl halide to a stirred mixture of aqueous cyanide salt and water-immiscible aprotic solvent. Although the reaction can be carried out over a wide temperature range, the range 0° C.–50° C. is satisfactory in most cases, and it is preferred to carry out the reaction at room temperature, since neither external heating nor cooling are then required.

The process will be understood more readily by reference to the following Examples, which illustrate it. Temperatures are in degrees Celsius. The reactions exemplified were, in many cases, monitored by gas liquid partition chromatography (glpc), and the time required for disappearance of the limiting reagent after beginning addition of the acyl halide was determined, together with the amount of alpha-cyano ester produced at that time.

EXAMPLE

Preparation of α-cyano-3-phenoxybenzyl 3-(2,2-dichloroethenyl)-2,2-dimethylcyclopropanecarboxylate using diazabicyclo[2.2.2]octane dihydrochloride as the rate-promoting agent (1) A flask was charged with 3-phenoxybenzaldehyde (1.98 g, 10.0 mmole) 10 ml n-heptane, diazabicyclo[2.2.2]octane dihydrochloride (30 mg, 0.2 mmole), sodium cyanide (0.59 g, 12 mmole), 1 ml water, and a solution of 3-(2,2-dichloroethenyl)-2,2-dimethylcyclopropanecarbonyl chloride (2.38 g, 10.5 mmole) in 10 ml n-heptane. The reaction mixture was stirred, and after 1.5 hours glpc indicated a 96% yield of the desired ester. After a total of 1 hr., 50 min, the reaction mixture was filtered, diluted with ether, the phases were separated, the ether phase was dried over magnesium sulfate, and the solvent was evaporated to afford the desired ester (3.98 g).

(2) A stirred mixture of sodium cyanide (18.1 g, 0.36 mole) and diazabicyclo[2.2.2]octane dihydrochloride (1.11 g, 0.006 mole) in 30 g of water was warmed to 40°. During a one hour period a solution of 3-(2,2-dichloroethenyl)-2,2-dimethylcyclopropanecarbonyl chloride (77.6 g, 0.33 mole) and 3-phenoxybenzaldehyde (61.5 g, 0.3 mole) in 102 ml of n-heptane was added to the reaction mixture. After complete addition, the reaction mixture was stirred for 40 minutes and an additional 3.5 g (0.015 mole) of the acyl chloride added. The reaction mixture was stirred for an additional 40 minutes and then washed with 100 g of a 10% aqueous sodium carbonate solution and then water. The organic phase was separated from the mixture and the solvent removed by distillation under reduced pressure to give α-cyano-3-phenoxybenzyl 3-(2,2-dichloroethenyl)-2,2-dimethylcyclopropanecarboxylate.

The preparation of α-cyano-3-phenoxybenzyl 3-(2,2-dichloroethenyl)-2,2-dimethylcyclopropanecarboxylate using other rate-promoting agents under otherwise similar conditions gave the following results.

| Rate-Promoting Agent | Reaction Time | Yield |
|---|---|---|
| 2,7-dimethyl-2,7-diazaoctane dihydrochloride | 1.4 hr | 96% |
| 2,3,4,6,7,8,10-octahydropyrimido [1,2-a]azepine hydrochloride | 4 hr | 99% |
| quinuclidine hydrochloride | 1.8 hr | 98% |

I claim:

1. A process for preparing an insecticidal α-cyano-3-phenoxybenzyl ester of the formula

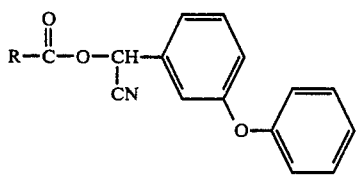

wherein R is selected from 3-(2,2-dichloroethenyl)-2,2-dimethylcyclopropyl, 3-(2,2-dibromoethenyl)-2,2-dimethylcyclopropyl, 3-(2-chloro-b 3,3,3-trifluoropropenyl)-2,2-dimethylcyclopropyl, 2,2,3,3-tetramethylcyclopropyl, and 1-(4-chlorophenyl)-2-methylpropyl which comprises reacting an acyl halide of the formula

wherein X is chlorine or bromine and R is as defined above with 3-phenoxybenzaldehyde in a mixture of substantially water-immiscible aprotic solvent and an aqueous solution of water-soluble cyanide salt in the presence of a catalytic amount of rate-promoting agent selected from acid salts of tertiary amines.

2. The process of claim 1 wherein the acid salts of tertiary amines are selected from products of the reaction of a strong acid and a linear tertiary polyamine of the formula

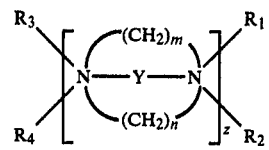

wherein Y is —$(CH_2)_k$— with k being 1-6, $C_3$-$C_7$ cycloalkane, $C_2$-$C_6$ alkenyl, or $C_2$-$C_6$ alkynyl; z is 1 or 2, and when z is 1, m and n are 0 or independently 1-6, and when m and n are 0, $R_1$, $R_2$, $R_3$, and $R_4$ are hydrocarbon groups, and $R_1$ may be joined with $R_2$, and $R_3$ may be joined with $R_4$ to form a ring containing the N atom to which both are joined, and when m is 1-6 and n is 0, $R_1$ and $R_3$ are absent, and $R_2$ and $R_4$ are hydrocarbon groups, and when both m and n are at least 1, $R_2$ and $R_4$ are absent; and when z is 2, m and n are 0, $R_1$ and $R_3$ are hydrocarbon groups and $R_2$ and $R^4$ are absent.

3. The process of claim 1 wherein the rate-promoting agent is selected from diazabicyclo[2.2.2]octane dihydrochloride, 2,7-dimethyl-2,7-diazaoctane dihydrochloride, 2,3,4,6,7,8,9,10-octahydropyrimido[1,2-a]azepine hydrochloride, and quinuclidine hydrochloride.

4. The process of claim 3 wherein the rate-promoting agent is diazabicyclo[2.2.2]octane dihydrochloride.

5. A process according to any one of claims 1, 2, 3, or 4 wherein R is 3-(2,2-dichloroethenyl)-2,2-dimethylcyclopropyl.

6. A process according to any one of claims 1, 2, 3, or 4 wherein the water-immiscible aprotic solvent is n-heptane.

7. A process according to any one of claims 1, 2, 3, or 4 wherein the water-soluble cyanide salt is sodium cyanide.

* * * * *

UNITED STATES PATENT AND TRADEMARK OFFICE
CERTIFICATE OF CORRECTION

PATENT NO. : 4,254,052
DATED : March 3, 1981
INVENTOR(S) : Jonathan S. Baum

It is certified that error appears in the above—identified patent and that said Letters Patent is hereby corrected as shown below:

Col. 5, line 29, "3-(2-chloro-b 3,3,3-trifluoropropenyl)" should read --3-(2-chloro-3,3,3-trifluoropropenyl)--.

Signed and Sealed this

Twenty-sixth Day of May 1981

[SEAL]

Attest:

RENE D. TEGTMEYER

Attesting Officer     Acting Commissioner of Patents and Trademarks